United States Patent
Mori et al.

(10) Patent No.: US 6,653,496 B1
(45) Date of Patent: Nov. 25, 2003

(54) METHOD FOR PRODUCING ACRYLONITRILE, CATALYST FOR USE THEREIN AND METHOD FOR PREPARING THE SAME

(75) Inventors: Kunio Mori, Yokohama (JP); Yutaka Sasaki, Kamakura (JP); Kenichi Miyaki, Yokohama (JP); Hirokazu Watanabe, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/110,061

(22) PCT Filed: Oct. 17, 2000

(86) PCT No.: PCT/JP00/07194

§ 371 (c)(1),
(2), (4) Date: Apr. 8, 2002

(87) PCT Pub. No.: WO01/28986

PCT Pub. Date: Apr. 26, 2001

(30) Foreign Application Priority Data

Oct. 18, 1999 (JP) .......................................... 11-295914

(51) Int. Cl.$^7$ ............................................. C07C 253/00
(52) U.S. Cl. ...................................... 558/308; 502/205
(58) Field of Search ........................... 558/308; 502/205

(56) References Cited

U.S. PATENT DOCUMENTS 5,059,573 A  * 10/1991  Sasaki et al. ............... 502/205

FOREIGN PATENT DOCUMENTS

| EP | 475351 | 3/1992 |
| WO | 99/54037 | 10/1999 |

* cited by examiner

*Primary Examiner*—Joseph K. McKane
*Assistant Examiner*—Robert Shiao
(74) *Attorney, Agent, or Firm*—Oblon, Spivak, McClelland, Maier & Neustadt, P.C.

(57) ABSTRACT

For the production of acrylonitrile by ammoxidation of propylene, there is provided a process capable of giving a high yield and maintaining such an effect for a long period of time.

In producing acrylonitrile by ammoxidation of propylene, a fluidized bed catalyst is used and the reaction is carried out while appropriately adding a molybdenum-containing material, wherein the fluidized bed catalyst, in which iron antimonate exists as a crystal phase, contains molybdenum, bismuth, iron, potassium, an M component, an N component and silica as essential components, and has a number of Mo/Me of from 0.8 to 1, wherein the Mo/Me is a number obtained by dividing the product 20 of a valence number of molybdenum as molybdic acid and an atomic ratio of molybdenum by the sum of respective products of respective valence numbers and atomic ratios of respective metal molybdate-producible metal elements other than iron antimonate, that is, bismuth, iron, potassium, the M component element, the N component element and a T component element.

14 Claims, No Drawings

METHOD FOR PRODUCING ACRYLONITRILE, CATALYST FOR USE THEREIN AND METHOD FOR PREPARING THE SAME

TECHNICAL FIELD

This application is a 371 of PCT/JP00/07194, filed Oct. 17, 2000.

The present invention relates to a catalyst suitably used for the production of acrylonitrile by ammoxidation of propylene, a process for producing said catalyst and a process for producing acrylonitrile by using said catalyst.

BACKGROUND ART

With respect to a catalyst suitably used for the production of acrylonitrile by ammoxidation of propylene, various catalysts are disclosed. In JP-B-38-17967, there is disclosed an oxide catalyst containing molybdenum, bismuth and iron, and in JP-B-38-19111, there is disclosed an oxide catalyst containing iron and antimony. After that, studies have been extensively continued to improve these catalysts. For example, in JP-B-51-33888, JP-B-55-56839, JP-B-5S8-2232, JP-B-61-26419, JP-A-7-47272, JP-A-10-43595, JP-A-4-11805 and the like, there are disclosed one improvement comprising using another component in addition to molybdenum, bismuth and iron, and the other improvement comprising using another component in addition to iron and antimony.

Further, in using these catalysts for the ammoxidation reaction, it is proposed to carry out said reaction while supplying a molybdenum-containing material thereto, thereby maintaining the catalyst efficiency. For example, in JP-B-58-57422, there is disclosed a process, wherein a particle formed by supporting a molybdenum-containing material on silica is supplied to a fluidized bed catalyst containing molybdenum, bismuth, iron, cobalt and others, thereby restoring the catalyst efficiency. In DE 3,311,521 and WO 97/33863, there is disclosed a process, wherein molybdenum trioxide or a molybdenum compound capable of converting to said trioxide in a specific amount is supplied to a catalyst similar to that mentioned above. Also with respect to a catalyst containing iron and antimony, there is known a similar proposal, for example, in JP-B-2-56938 and JP-B-2-56939.

These catalysts of the prior arts were effective to improve a yield of acrylonitrile at an early stage. However, these catalysts have been still insufficient in respect to repeatability in the production thereof, structural stability and long-term stability of the ammoxidation yield of desired products. Also with respect to a catalyst containing iron and antimony, particularly a molybdenum component-enriched catalyst containing a crystal phase of iron antimonate, which is disclosed in JP-A-4-118051, it has been very important to improve those from an industrial point of view and therefore further investigation of these catalysts have been required.

In addition, also with respect to the process comprising supplying the molybdenum component to maintain the catalyst efficiency, it is difficult to say that it is always effective. Even if the molybdenum-containing material is supplied, no effect can be observed in the case where a catalyst structure is markedly damaged. Further, even if loss of molybdenum is not so large, no effect can be exhibited in the case where lowering of the catalyst efficiency is mainly caused by change of the catalyst structure. It is finding that the catalyst to be applied itself should be stable and should have no extreme damage on its structure.

It has been desired to find a catalyst, which is capable of further improving the acrylonitrile yield, stable when used for the ammoxidation reaction, and capable of maintaining its efficiency for a long period of time by the supply of a molybdenum-containing material. An object of the present invention is particularly to improve a process for producing acrylonitrile and to solve these problems. More specifically, an object of the present invention is to improve the catalyst composition disclosed in JP-A-4-118051, thereby giving a catalyst more suitably used for the production of acrylonitrile by fluidized bed ammoxidation reaction. Another object of the present invention is also to improve reaction processes disclosed in JP-B-2-56938 and JP-B-2-56939.

DISCLOSURE OF INVENTION

The present inventors have undertaken extensive studies to solve the above-mentioned problems. As a result, they found that the object can be effectively accomplished by providing a fluidized bed catalyst, which comprises iron antimonate, molybdenum, bismuth, iron, potassium, an M component and an N component as essential components, and which has an Mo/Me of from 0.8 to 1, wherein the Mo/Me is a number obtained by dividing the product (Mo: 20) of a valence number of molybdenum as molybdic acid and an atomic ratio of molybdenum by the sum (Me) of respective products of respective valence numbers and atomic ratios of respective metal molybdate-producible metal elements other than iron antimonate, namely bismuth, iron, potassium and M, N and T component elements. Further they found that the object can be effectively accomplished by carrying out the ammoxidation reaction while appropriately adding a molybdenum-containing material to said catalyst.

The present catalyst composition is capable of giving a high acrylonitrile yield. Moreover, the catalyst is stable in its catalyst structure, and so resistant to use of a long-term reaction. When the Mo/Me exceeds the above-defined range, an excess molybdenum component may enter the interface of metal molybdate, which functions as a catalyst, and as a result, any dysfunction may be caused, or undesired reaction with the iron antimonate may be caused. Whereas, when the Mo/Me is less than the above-defined range, the acrylonitrile yield decreases and at the same time variation with the lapse of time becomes large.

Still, in the case where even such a catalyst is used without interruption for the ammoxidation reaction, a decrease of the acrylonitrile yield due to escaping of the molybdenum component may be observed. Since the ammoxidation reaction is carried out at a temperature exceeding 400° C., it seems that the escaping of the molybdenum component at the time of reaction is inevitable in this kind of catalyst having a large molybdenum content. In this regard, the acrylonitrile yield was able to be maintained at a high degree for a long period of time by continuing the reaction while adding the molybdenum-containing material.

According to the catalyst in accordance with the present invention, which is structurally stable, the yield of desired products can be more sufficiently restored by appropriately adding the molybdenum-containing material at the time of the ammoxidation reaction. Moreover, since the addition of the molybdenum-containing material at the time of the ammoxidation reaction can be repeated, the catalyst in accordance with the present invention can be used for a much longer period of time by such a repeated addition of the molybdenum-containing material. The addition of the molybdenum-containing material may be carried out from an early stage of the reaction. In applying the catalyst to the ammoxidation reaction, it is general that a catalyst surface composition is optimized by means of a composition, a preparation method or the like. However, it is difficult to say that the optimization can be always realized. As the case may be, the yield of the desired product increases by addition of the molybdenum-containing material at the start of the reaction. This seems that the optimization of the catalyst surface composition and the structure thereof can be realized also with the aid of the molybdenum-containing material.

With respect to a conventional catalyst, the acrylonitrile yield has been insufficient, and it has been insufficient to restore the catalyst efficiency even if the molybdenum-containing material is added on the grounds that the yield decreases owing to a long-term use. According to the present invention, there is provided a process capable of maintaining a high acrylonitrile yield for a long period of time.

That is, the present invention provides a process for producing acrylonitrile, which comprises using a fluidized bed catalyst of a composition represented by the following empirical formula in the production of acrylonitrile by ammoxidation of propylene. The present invention also provides a process for producing acrylonitrile according to said process, wherein the ammoxidation reaction is carried out while appropriately supplying a molybdenum-containing material. Further, the present invention provides said fluidized bed catalyst and a process for producing said fluidized bed catalyst.

$(Fe\ Sb_a)_b\ Mo_{10}\ Bi_c\ Fe_d\ K_k\ M_m\ N_n\ G_g\ Q_q\ R_r\ T_t\ O_x\ (SiO_2)_y$

In the formula, (Fe Sba) represents iron and antimony forming iron antimonate; Mo, Bi, Fe and K are molybdenum, bismuth, iron and potassium, respectively; M is at least one element selected from the group consisting of magnesium, calcium, strontium, barium, manganese, cobalt, nickel, copper, zinc and cadmium, in which group preferred are magnesium, calcium, manganese, cobalt, nickel and zinc; N is at least one element selected from the group consisting of chromium, yttrium, lanthanum, cerium, praseodymium, neodymium, samarium, aluminum, gallium and indium, preferably a combination of two elements selected therefrom, more preferably a combination of chromium and the other, in which group preferred are chromium, lanthanum, cerium, praseodymium, neodymium, samarium, aluminum and indium; G is at least one element selected from the group consisting of ruthenium, rhodium, palladium, rhenium, osmium, iridium, platinum and silver, in which group preferred are ruthenium, palladium and silver; Q is at least one element selected from the group consisting of titanium, zirconium, vanadium, niobium, tantalum, tungsten, germanium, tin, lead and antimony, in which group preferred are zirconium, vanadium, niobium, tungsten, germanium, tin and antimony; R is at least one element selected from the group consisting of boron, phosphorus and tellurium; T is at least one element selected from the group consisting of lithium, sodium, rubidium, cesium and thallium, in which group preferred are rubidium and cesium; O is oxygen; Si is silicon; and affixes a, b, c, d, k, m, n, g, q, r, t, x and y are independently of one another an atomic ratio, provided that a=0.8 to 2, preferably 0.85 to 1.8, more preferably 0.9 to 1.5, b=0.5 to 20, preferably 0.7 to 15, more preferably 1 to 7, c=0.1 to 2, preferably 0.2 to 1.5, more preferably 0.3 to 1, d 0.3 to 3, preferably 0.5 to 2.5, more preferably 0.8 to 2, k=0.05 to 2, preferably 0.1 to 1.5, more preferably 0.1 to 0.8, m=3 to 8, preferably 4 to 7, more preferably 5 to 6.5, n=0.1 to 3, preferably 0.2 to 2.5, more preferably 0.3 to 2.5, g=0 to 0.5, preferably 0 to 0.2, more preferably 0 to 0.1, q=0 to 3, preferably 0 to 2, more preferably 0 to 1, r=0 to 3, preferably 0 to 2, more preferably 0 to 1, t=0 to 1, preferably 0 to 0.5, more preferably 0 to 0.2, x is a number of oxygen in a metal oxide formed by bonding of said respective components, y=20 to 200, preferably 25 to 80, more preferably 35 to 60; and a number of Mo/Me is from 0.8 to 1, wherein the Mo/Me is a number obtained by dividing the product, which is 20, of a valence number of molybdenum as molybdic acid and an atomic ratio of molybdenum by the sum of respective products of respective valence numbers and atomic ratios of respective metal molybdate-producible metal elements other than iron antimonate, that is, bismuth, iron, potassium, the M component element, the N component element and the T component element.

Embodiments of the present invention are explained in more detail as follows.

It is essential that iron antimonate exists as a crystal phase in the present catalyst, and molybdenum, bismuth, iron, potassium, the M component, the N component and silica ($SiO_2$) are contained therein. If these components are not used in the above-defined composition range, the objects of the present invention cannot be accomplished. The iron antimonate is a compound represented by a chemical formula, $FeSbO_4$, as disclosed in the above-mentioned JP-A-4-118051 and JP-A-10-231125, and the existence thereof can be confirmed by an X-ray diffraction of the catalyst. The iron antimonate is essential for improving an unsaturated nitrile yield and for qualification of physical properties of the catalyst.

Bismuth can serve to exhibit a superior catalyst efficiency in a relatively small composition region. Generally speaking, in the case where the iron component excluding that contained in iron antimonate is too large, the acrylonitrile yield increases. On the other hand, when it is too little, an acrylonitrile selectivity at an early stage of the reaction increases, but long-term stability deteriorates. The M component serves for stabilization of the catalyst structure. As the M component, particularly preferred are magnesium, calcium, manganese, cobalt, nickel and zinc. The N component also serves for stabilization of the catalyst structure. As the N component, preferred are chromium, lanthanum and cerium. Particularly preferred is a component containing two elements of said elements, and more preferred is to use both chromium and the other element.

As the catalyst components, the above-mentioned T component may be further incorporated. The T component serves to control acidity of the catalyst like the potassium component, and acts to improve an acrylonitrile selectivity and to control the production of by-products. As the T component, particularly preferred are rubidium and cesium.

As the catalyst components, the above-mentioned G, Q and R components may be further incorporated. As the case may be, these can be added for the purpose of stabilization of the catalyst structure, improvement of oxidation reduction characteristics, control of acidity and basicity and others. As the G component, preferred are palladium, ruthenium and silver. As the Q component, preferred are zirconium, vanadium, niobium, tungsten, germanium, tin and antimony. If desired, the R component may be added in a small amount for the purpose of improving the acrylonitrile selectivity, controlling by-products or others.

The process for producing acrylonitrile in accordance with the present invention is carried out according to a fluidized bed reaction. Accordingly, the catalyst is additionally required to have physical properties suitable for the fluidized bed reaction. That is, it is additionally required that its bulk density, particle strength, attrition resistance, specific surface area, fluidity and others are suitable. For that purpose, silica is used as a carrier component.

In obtaining the catalyst, the starting iron antimonate and the other metal molybdate-producible metal elements, that is, bismuth, iron, potassium, the M and N component materials and the molybdenum component material, and if desired, the T component material are blended, and the resulting blend is subjected to spray-drying and calcination. In this regard, it is important that the blend is carried out so as to obtain a catalyst having the number obtained by dividing Mo by Me, namely Mo/Me, of from 0.8 to 1, provided that the valence numbers of bismuth, iron and the N component element are assigned to be 3, respectively, that of the M component is assigned to be 2, those of potassium and the T component are assigned to be 1, respectively, the product (Mo) of the valence number (2) of molybdenum as molybdic acid $((MoO_4)^{2-})$ and the atomic ratio thereof (10) is 20 (=2×10), and the sum of respective products of respective valence numbers and atomic ratios of the other metal molybdate-producible metal elements, that is, bismuth, iron, potassium and the M, N and T component elements, is Me (:3c+3d+k+2m+3n+t).

For preparing iron antimonate, various processes are proposed. For example, there are processes disclosed in JP-A-4-118051 and JP-A-10-231125, and a process to be applied may be selected therefrom. In the production of the catalyst in accordance with the present invention, it is important that iron antimonate is prepared in advance, and thereafter is mixed with other catalyst component materials. The iron antimonate prepared may contain a small amount of an element other than antimony and iron. The existing iron antimonate serves for the improvement of acrylonitrile selectivity and physical properties of the fluidized bed catalyst.

The thus prepared iron antimonate is blended with other component materials. In this regard, from a viewpoint of obtaining a preferred catalyst structure in the composition region where bismuth and iron are little like in the catalyst composition in accordance with the present invention, it is important that the aforesaid Mo/Me value is taken as from 0.8 to 1. This kind of the catalyst is composed of multiple layers, which have to be systemically related to one another. However, when the Mo/Me ratio is less than 0.8, the metal elements, which are to be counter ions of the molybdic acid, do not form any molybdate, but only their oxides or others. As a result, it is easy to deteriorate selectivity of the desired product in the catalytic reaction. It is finding that it is difficult to build a satisfactory relation between said multiple layers in a composition region where the Mo/Me ratio exceeds 1. It seems that this is one of reasons why the repeatability in the production of the catalyst is deteriorated in a conventional composition region. It also seems that when the ratio exceeds 1, free molybdenum is converted into its oxide, which goes between the layers to cause inhibition of the catalytic function or brings about an undesirable reaction with iron antimonate during the preparation of the catalyst.

For preparing the catalyst in accordance with the present invention, it is permitted to select a process to be applied from processes disclosed in the above-mentioned prior arts.

Materials used for the molybdenum component include molybdenum oxide and ammonium paramolybdate, wherein ammonium paramolybdate is preferably used. Materials used for the bismuth component include bismuth oxide, bismuth nitrate, bismuth carbonate and bismuth oxalate, wherein bismuth nitrate is preferably used. Materials used for the iron components include iron nitrate such as ferrous nitrate (iron (II) nitrate) and ferric nitrate (iron (III) nitrate), and iron oxalate such as ferrous oxalate (iron (II) oxalate) and ferric oxalate (iron (III) oxalate), wherein preferred is the iron nitrate. Materials used for the potassium component include potassium nitrate and potassium hydroxide, wherein preferred is potassium nitrate, Materials of the M, N, G and T components include respective oxides, hydroxides and nitrates, wherein preferred are nitrates. Materials of the Q component include respective oxides, hydroxides, nitrates and oxygen acids or salts thereof. With respect to materials of the R component, materials used for boron include boric acid and anhydrous boric acid, wherein anhydrous boric acid is preferably used, materials used for phosphorus include phosphoric acid such as orthophosphoric acid, and materials used for tellurium include metal tellurium, tellurium dioxide, tellurium trioxide and telluric acid. Materials used for silica include silica sol and fumed silica. It is convenient to use silica sol.

The iron antimonate is blended with other component materials to obtain a slurry. These catalyst materials are blended, and thereafter the resulting mixture is subjected to spray drying and calcination to obtain a desired fluidized bed catalyst. The catalyst materials are blended and, if necessary pH of the slurry was adjusted, and the resulting slurry is subjected to heat treatment and others thereby to be able to prepare a catalyst slurry. In preparing the catalyst slurry, preparation conditions such as a mixing means of the materials, temperature, pressure and atmosphere can be voluntarily determined. When the slurry is prepared by adjusting pH of the slurry to a relatively high degree such as 3 to 8, it is recommendable to add a chelating agent such as ethylenediamine tetraacetate, lactic acid, citric acid, tartaric acid and gluconic acid according to a process disclosed in Japanese Patent No. 2747920, thereby preventing the slurry from gelling. In the case where the pH is adjusted to a relatively low degree such as 1 to 3 to prepare it, it is not always necessary to add the chelating agent. However, when added in a small amount, good result may be obtained.

The thus prepared slurry can be dried by means of spray drying. A spray drying apparatus is not particularly limited, and may be a conventional one such as a rotary-disk type and a nozzle type. A slurry concentration of the slurry entering the spray drying apparatus is preferably from about 10 to about 40% by weight in terms of an oxide of the element constituting the catalyst. The catalyst materials can be granulated by means of the spray drying. A spray drying temperature is not particularly limited. In carrying out the spray drying, pressure and atmosphere can be voluntarily determined. These spray-drying conditions are determined so as to obtain a catalyst having a desired particle diameter as a fluidized bed catalyst.

After completion of the drying, calcination can be carried out to obtain a desired fluidized bed catalyst. In carrying out the calcination, calcination conditions such as a calcination means, temperature, pressure and atmosphere can be voluntarily determined. For example, the calcination can be carried out at 200 to 500° C., and additionally at 500 to 700° C. for 0.1 to 20 hours. A calcination atmosphere is preferably an oxygen containing gas. It is conveniently carried out in air, which may be used in combination with a combination of oxygen and nitrogen, carbonic acid gas, water vapor or the like. For the calcination, a box type calciner, a tunnel type calciner, a rotary calciner, a fluidized bed calciner and others can be used. It is recommendable to adjust a particle diameter of the thus obtained fluidized bed catalyst to preferably from 5 to 200 µm, more preferably from 20 to 150 µm. Incidentally, the particle diameter used herein is not an average particle diameter of the whole particles, but a particle diameter of the individual particles.

In using the molybdenum-containing fluidized bed catalyst for the production of acrylonitrile, as mentioned above, it is known that the molybdenum-containing material is added during the reaction, thereby maintaining the yield of the desired product. However, such an effect cannot be expected to a sufficient extent unless such a process is applied to a catalyst having a stable catalyst structure. Since the catalyst in accordance with the present invention is relatively structurally stable even when used for a long period of time at a temperature exceeding 400° C., at which this kind of the ammoxidation reaction is carried out, the reaction can be continued while adding the molybdenum-containing material, thereby maintaining the yield of desired products equal or superior to those of the early stage. However, even when such a structurally stable catalyst is used, the molybdenum component evaporates little by little from the catalyst under a reaction condition, and maybe this causes damage of the catalyst structure. Accordingly, when the molybdenum-containing material is supplied, it is necessary that the molybdenum-containing material be supplied before it becomes impossible to restore such a damage of the catalyst structure.

The molybdenum-containing material used here includes metal molybdenum, molybdenum trioxide, molybdic acid, ammonium dimolybdate, ammonium paramolybdate, ammonium octamolybdate, ammonium dodecamolybdate, phosphomolybdic acid, and those obtained by supporting these molybdenum-containing material with an inert substance or the above-mentioned catalyst. Of these, preferred are molybdenum trioxide, ammonium paramolybdate and those obtained by supporting these molybdenum-containing materials with an inert substance or the above-mentioned catalyst. Although the molybdenum-containing material can be used in a gaseous state or a liquid state, it is preferred from a practical point of view that these solid molybdenum-containing materials are used in a powder state. It is particularly effective to apply a process comprising using a molybdenum-enriched catalyst obtained by enriching the above-mentioned catalyst with the molybdenum-containing material. According to the process, molybdenum in the molybdenum-containing material added can be efficiently utilized, and troubles caused by precipitation of the molybdenum oxide in the system or other reasons can be avoided. For preparing the molybdenum-enriched catalyst, the process described in JP-A-11-33400 or the like can be applied.

These molybdenum-containing materials may be added in a reactor in a continuous or intermittent manner at intervals. The time of addition and an amount to be added may be appropriately determined depending upon the yield of desired products. The amount added at a time is preferably from 0.01 to 3% by weight, more preferably from 0.05 to 2% by weight, as molybdenum element based on the weight of the catalyst filled in a reactor. It is necessary to pay attention to the followings. When the molybdenum-containing material is added in a large amount in a time, it may happen that the substance wastefully escapes out of the reaction system, thereby resulting in useless consumption, and moreover the material precipitates or accumulates inside of the reactor or adheres to a heat exchanger, thereby causing operational problems.

The ammoxidation of propylene is usually carried out at a reaction temperature of 370 to 500° C. under a reaction pressure of from atmospheric pressure to 500 kPa using a feeding gas having a composition of propylene/ammonia/oxygen=1/0.9 to 1.3/1.6 to 2.5 (molar ratio). An apparent contact time is usually from 0.1 to 20 seconds. It is convenient to use air as an oxygen source, which air may be diluted with water vapor, nitrogen, carbonic acid gas, a saturated hydrocarbon or the like, or may be enriched with oxygen.

BEST MODE FOR CARRYING OUT INVENTION

The present invention is explained in more detail with reference to Examples and Comparative Examples, which are not intended to limit the scope of the present invention.

DETERMINATION OF CATALYST ACTIVITY

Synthesis of acrylonitrile by means of ammoxidation of propylene was carried out as follows to evaluate the catalyst activity.

A catalyst was filled in a fluidized bed reactor having a catalyst fluidizing zone of an inner diameter of 25 mm and a height of 400 mm, and a mixed gas having a composition of propylene/ammonia/air/water vapor=1/1.2/9.5/0.5 (molar ratio) was introduced therein at a linear velocity of the gaseous feedstock of 4.5 cm/sec. The reaction pressure was controlled to 200 kPa.

Still, at the time of reaction, a molybdenum-containing material was appropriately added. The molybdenum-containing material such as some molybdenum compounds and molybdenum component-enriched catalysts was added, at intervals of 100 to 500 hours, in an amount of 0.1 to 0.2% by weight as molybdenum element based on the weight of the catalyst filled in a reactor. The molybdenum-containing material, which was in a powder state, was fed from an upper part of the reactor.

Contact time and the acrylonitrile yield were found according to the following calculation equations, respectively.

Contact time (sec)=Volume of catalyst (ml) based on apparent bulk density/Flow rate of feeding gas converted to reaction conditions (ml/sec).

Acrylonitrile yield (%)=Mole number of acrylonitrile produced/Mole number of propylene supplied×100.

EXAMPLE 1

A catalyst of a composition, $Fe_3Sb_{3.3}Mo_{10}Bi_{0.4}Fe_{1.3}K_{0.2}Ni_6Cr_{0.8}Ce_{0.4}P_{0.2}B_{0.2}O_x(SiO_2)_{35}$ (x is a number naturally determined depending upon the valence numbers of the other elements), was prepared as follows.

In 3000 g of pure water, 346.5 g of ammonium paramolybdate was dissolved, and successively 3.3 g of 85% phosphoric acid and 1.4 g of anhydrous boric acid were independently added thereto. The resulting liquid was mixed with another liquid obtained by dissolving 38.1 g of bismuth nitrate, 4.0 g of potassium nitrate, 342.5 g of nickel nitrate, 62.8 g of chromium nitrate, 34.1 g of cerium nitrate and 25.0 g of citric acid in 270 g of 3.3% nitric acid. A liquid obtained by dissolving 103.1 g of ferric nitrate and 25.0 g of citric acid in 270 g of pure water was prepared and added to the mixture. Successively, 2064.0 g of 20% silica sol was added thereto. The resulting slurry was adjusted to pH 2 by addition of 15% aqueous ammonia while being stirred, and subjected to heat treatment at 98° C. for 1.5 hours. Further, 733.0 g of 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 660° C. for 3 hours.

Incidentally, the iron antimonate slurry used was prepared as follows.

To a mixture of 1110.1 g of 65% by weight nitric acid and 615.3 g of pure water, 133.3 g of electrolytic iron powder was added little by little. After the iron powder was completely dissolved, 384.7 g of antimony trioxide powder was added thereto, and then 10% aqueous ammonia was dropwise added thereto to adjust the pH to 1.8 while being stirred. The resulting slurry was heated at 98° C. for 3 hours under stirring. The slurry was dried using a spray drier, whose inlet temperature and outlet temperature were controlled to 330° C. and 160° C., respectively, and the dried product was subjected to calcination at 250° C. for 2 hours and additionally at 400° C. for 2 hours, and further subjected to calcination at 850° C. for 3 hours under nitrogen atmosphere. After completion of calcination, the product was pulverized, followed by mixing with pure water, thereby obtaining the 20% iron antimonate slurry. In the following Examples and Comparative Examples also, the iron antimonate slurry prepared in such a manner was used.

EXAMPLE 2

A catalyst having a composition of $Fe_3Sb_{3.3}Mo_{10}Bi_{0.4}Fe_{1.1}K_{0.3}Ni_4Co_2Cr_{0.8}Ce_{0.5}P_{0.2}O_x(SiO_2)_{35}$ was prepared in a manner similar to that of Example 1, and then subjected to calcination under conditions as shown in Table 1, except that no anhydrous boric acid was added and cobalt nitrate as a Co material additionally dissolved in the above-mentioned nitric acid was added.

EXAMPLE 3

A catalyst having a composition of $Fe_3Sb_{3.3}Mo_{10}Bi_{0.4}Fe_{1.3}K_{0.2}Ni_{5.5}Zn_{0.2}Cr_{3.5}Ce_{0.6}La_{0.2}Ge_{0.2}B_{0.2}O_x(SiO_2)_{35}$ was prepared in a manner similar to that of Example 1, and then subjected to calcination under conditions as shown in Table 1, except that no phosphoric acid was added, and lanthanum nitrate and zinc nitrate as a La material and a Zn material, respectively, additionally dissolved in the above-mentioned nitric acid, and germanium oxide as a Ge material were independently added next to the addition of ammonium paramolybdate.

EXAMPLE 4

A catalyst having a composition of $Fe_3Sb_{3.3}Mo_{10}Bi_{0.3}Fe_{1.5}K_{0.2}Ni_5Mg_1Cr_{0.5}Ce_{0.3}Pr_{0.2}O_x(SiO_2)_{35}$ was prepared in a manner similar to that of Example 1, and then subjected to calcination under conditions as shown in Table 1, except that phosphoric acid and anhydrous boric acid were not added and praseodymium nitrate and magnesium nitrate as a Pr material and an Mg material, respectively, additionally dissolved in the above-mentioned nitric acid were added.

EXAMPLE 5

A catalyst having a composition of $Fe_3Sb_{3.3}Mo_{10}Bi_{0.5}Fe_{1.3}K_{0.1}Ni_{5.75}Mn_{0.5}Cr_{0.8}Ce_{0.75}Pd_{0.01}Rb_{0.01}P_{0.1}B_{0.1}O_x(SiO_2)_{40}$ was prepared as follows.

In 3000 g of pure water, 321.1 g of ammonium paramolybdate was dissolved, and successively 1.53 g of 85% phosphoric acid and 0.6 g of anhydrous boric acid were added thereto. The resulting liquid was mixed with another liquid obtained by dissolving 44.1 g of bismuth nitrate, 1.8 g of potassium nitrate, 304.1 g of nickel nitrate, 26.1 g of manganese nitrate, 58.2 g of chromium nitrate, 59.2 g of cerium nitrate, 0.4 g of palladium nitrate, 2.7 g of rubidium nitrate and 25 g of citric acid in 270 g of 3.3% nitric acid. Successively, 2185.5 g of 20% silica sol was added thereto. Thereafter, the resulting mixture was adjusted to pH 7.7 by dropwise-addition of 15% aqueous ammonia while being stirred, and subjected to heat treatment at 98° C. for 1.5 hours. A liquid obtained by dissolving 95.5 g of ferric nitrate and 25 g of citric acid in 270 g of pure water was added thereto. Further, 679.5 g of a 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 670° C. for 3 hours.

EXAMPLE 6

A catalyst having a composition of $Fe_3Sb_{3.3}Mo_{10}B_{0.8}Fe_{1.3}K_{0.2}Ni_{5.5}Cr_{0.8}Ce_{0.4}In_{0.2}W_{0.5}\ P_{0.2}O_x(SiO_2)_{60}$ was prepared as follows.

In 3000 g of pure water, 19.2 g of ammonium paratungstate and thereafter 260 g of ammonium paramolybdate were dissolved, and successively 2.47 g of 85% phosphoric acid was added thereto. The resulting liquid was mixed with another liquid obtained by dissolving 57.2 g of bismuth nitrate, 3 g of potassium nitrate, 235.6 g of nickel nitrate, 47.1 g of chromium nitrate, 25.6 g of cerium nitrate, 3.48 g of indium nitrate and 25 g of citric acid in 270 g of 3.3% nitric acid. Successively, 2655.1 g of 20% silica sol was added thereto. The resulting slurry was adjusted to pH 5 by dropwise-addition of 15% aqueous ammonia while being stirred, and subjected to heat treatment under reflux at 98° C. for 1.5 hours. A liquid prepared by dissolving 77.4 g of ferric nitrate and 25 g of citric acid in 270 g of pure water was added thereto. Further, 550 g of a 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 670° C. for 3 hours.

EXAMPLE 7

A catalyst having a composition of $Fe_3Sb_{3.3}Mo_{10}Bi_{0.5}Fe_2K_{0.2}Ni_4Mg_{1.5}Cr_{0.5}Ce_{0.5}\ Al_{0.1}Nb_{0.1}O_x(SiO_2)_{35}$ was prepared in a manner similar to that of Example 6, and then subjected to calcination under conditions as shown in Table 1, except that ammonium paratungstate, phosphoric acid and indium nitrate were not added, and aluminum nitrate and magnesium nitrate as an Al material and an Mg material, respectively, additionally dissolved in the above-mentioned nitric acid, and niobium hydrogen oxalate as an Nb material were independently added next to the addition of ammonium paramolybdate.

EXAMPLE 8

A catalyst having a composition of $Fe_{1.5}Sb_{1.7}Mo_{10}Bi_{0.5}Fe_1K_{0.2}Ni_{Co1.5}Cr_2Ce_{0.5}Ru_{0.05}\ Cs_{0.05}P_{0.3}O_x(SiO_2)_{35}$ was prepared in a manner similar to that of Example 6, and then subjected to calcination under conditions as shown in Table 1, except that ammonium paratungstate and indium nitrate were not added, and cobalt nitrate and cesium nitrate as a Co material and a Cs material, respectively, additionally dissolved in the above-mentioned nitric acid, and ruthenium oxide as an Ru material were independently added next to the addition of ammonium paramolybdate.

EXAMPLE 9

A catalyst having a composition of $Fe_5Sb_{5.5}Mo_{10}Bi_{0.5}Fe_{1.3}K_{0.2}Ni_6\ Cr_1Ce_{0.2}Nd_{0.2}Zr_{0.2}P_{0.1}O_x(SiO_2)_{35}$ was prepared in a manner similar to that of Example 6, and then subjected to calcination under conditions as shown in Table 1, except that ammonium paratungstate and indium nitrate were not added, and neodymium nitrate and zirconium nitrate as an Nd material and a Zr material, respectively, additionally dissolved in the above-mentioned nitric acid were added.

EXAMPLE 10

A catalyst having a composition of $Fe_7Sb_{7.7}Mo_{10}Bi_{0.5}Fe_{1.2}K_{0.2}Ni_{5.75}Cr_{1.5}Ce_{0.5}Sm_{0.2}V_{0.1}Te_{0.25}\ O_x(SiO_2)_{35}$ was prepared in a manner similar to that of Example 6, and then subjected to calcination under conditions as shown in Table 1, except that ammonium paratungstate, phosphoric acid and indium nitrate were not added, and samarium nitrate as a Sm material additionally dissolved in the above-mentioned nitric acid, and ammonium methavanadate as a V material were independently added next to the addition of ammonium paramolybdate, and moreover a liquid obtained by dissolving telluric acid as a Te material in water was added to the solution of ferric nitrate and citric acid.

COMPARATIVE EXAMPLE 1

A catalyst having a composition of $Fe_3Sb_{3.3}Mo_{10}Bi_{0.4}Fe_{0.6}K_{0.2}Ni_6Cr_{0.8}Ce_{0.4}P_{0.2}B_{0.2}O_x(SiO_2)_{35}$ prepared in a manner similar to that of Example 1, and then subjected to calcination under conditions as shown in Table 1, except that the amount of ferric nitrate was changed.

COMPARATIVE EXAMPLE 2

A catalyst having a composition of $Fe_3Sb_{3.3}M_{10}Bi_{0.4}Fe_{1.1}K_{0.2}Ni_6\ P_{0.2}B_{0.2}O_x(SiO_2)_{35}$ was prepared in a manner similar to that of Example 1, and then subjected to calcination under conditions as shown in Table 1, except that chromium nitrate and cerium nitrate were not added.

COMPARATIVE EXAMPLE 3

A catalyst having a composition of $Fe_3Sb_{3.3}Mo_{10}Bi_1Fe_{1.3}K_{0.2}Ni_{5.5}Zn_{0.2}Cr_{1.5}Ce_{0.6}La_{0.2}Ge_{0.2}B_{0.2}O_x(SiO_2)_{35}$ was prepared in a manner similar to that of Example 6, and then subjected to calcination under conditions as shown in Table 1, except that ammonium paratungstate, phosphoric acid and indium nitrate were not added, and lanthanum nitrate and zinc nitrate as a La material and a Zn material, respectively additionally dissolved in the above-mentioned nitric acid, anhydrous boric acid as a B material and germanium oxide as a Ge material were independently added next to the addition of ammonium paramolybdate.

COMPARATIVE EXAMPLE 4

A catalyst having a composition of $Fe_3Sb_{3.3}Mo_{10}Bi_{0.4}Fe_2K_{0.2}Ni_6Zn_{0.2}Cr_{1.5}Ce_{0.6}La_{0.2}Ge_{0.2}B_{0.2}O_x(SiO_2)_{35}$ was prepared in a manner similar to that of Example 6, and then subjected to calcination under conditions as shown in Table 1, except that ammonium paratungstate, phosphoric acid and indium nitrate were not added, and lanthanum nitrate and zinc nitrate as a La material and a Zn material, respectively, additionally dissolved in the above-mentioned nitric acid, anhydrous boric acid as a B material and germanium oxide as a Ge material were independently added next to the addition of ammonium paramolybdate.

Incidentally, the molybdenum-enriched catalysts used for the ammoxidation reaction in Examples 3 and 7 to 10 and Comparative Examples 3 and 4 were those prepared by impregnating the catalysts obtained in the corresponding Examples and Comparative Examples with an aqueous solution of ammonium paramolybdate, followed by drying and calcination.

Using the catalysts obtained in these Examples and Comparative Examples, the ammoxidation reaction of propylene was carried out under the foregoing conditions. The results were as shown in the following Table.

TABLE 1

| | Catalyst composition (atomic ratio) | | | | | | | | | | | | | |
|---|---|---|---|---|---|---|---|---|---|---|---|---|---|---|
| | FeSb | | | | | | | | | | | | | |
| | Fe | Sb | Mo | Bi | Fe | K | M | | N | | G | Q | R | T | SiO$_2$ | Mo/Me |
| Example 1 | 3 | 3.3 | 10 | 0.4 | 1.3 | 0.2 | Ni 6 | | Cr 0.8 Ce 0.4 | | | | P 0.2 B 0.2 | | 35 | 0.96 |
| Example 2 | 3 | 3.3 | 10 | 0.4 | 1.1 | 0.3 | Ni 4 Co 2 | | Cr 0.8 Ce 0.5 | | | | P 0.2 | | 35 | 0.97 |
| Example 3 | 3 | 3.3 | 10 | 0.4 | 1.3 | 0.2 | Ni 5.5 Zn 0.2 | | Cr 1.5 Ce 0.6 La 0.2 | | Ge 0.2 | | B 0.2 | | 35 | 0.85 |
| Example 4 | 3 | 3.3 | 10 | 0.3 | 1.5 | 0.2 | Ni 5 Mg 1 | | Cr 0.5 Ce 0.8 Pr 0.2 | | | | | | 35 | 0.97 |
| Example 5 | 3 | 3.3 | 10 | 0.5 | 1.3 | 0.1 | Ni 5.75 Mn 0.5 | | Cr 0.8 Ce 0.75 | | Pd 0.01 | | P 0.1 B 0.1 | Rb 0.1 | 40 | 0.88 |

TABLE 1-continued

| | | | | | | | | | | | | | | | | | | | | |
|---|---|---|---|---|---|---|---|---|---|---|---|---|---|---|---|---|---|---|---|---|
| Example 6 | 3 | 3.3 | 10 | 0.8 | 1.3 | 0.2 | Ni | 5.5 | Cr | 0.8 | | | W | 0.5 | P | 0.2 | | | 60 | 0.92 |
| | | | | | | | | | Ce | 0.4 | | | | | | | | | | |
| | | | | | | | | | In | 0.2 | | | | | | | | | | |
| Example 7 | 3 | 3.3 | 10 | 0.5 | 2 | 0.2 | Ni | 4 | Cr | 0.5 | | | Nb | 0.1 | | | | | 35 | 0.91 |
| | | | | | | | Mg | 1.5 | Ce | 0.5 | | | | | | | | | | |
| | | | | | | | | | Al | 0.1 | | | | | | | | | | |
| Example 8 | 1.5 | 1.7 | 10 | 0.5 | 1 | 0.2 | Ni | 4 | Cr | 2 | Ru | 0.05 | | | P | 0.3 | Cs | 0.05 | 35 | 0.86 |
| | | | | | | | Co | 1.5 | Ce | 0.5 | | | | | | | | | | |
| Example 9 | 5 | 5.5 | 10 | 0.5 | 1.3 | 0.2 | Ni | 6 | Cr | 1 | | | Zr | 0.2 | P | 0.1 | | | 35 | 0.92 |
| | | | | | | | | | Ce | 0.2 | | | | | | | | | | |
| | | | | | | | | | Nd | 0.2 | | | | | | | | | | |
| Example 10 | 7 | 7.7 | 10 | 0.5 | 1.2 | 0.2 | Ni | 5.75 | Cr | 1.5 | | | V | 0.1 | Te | 0.25 | | | 35 | 0.85 |
| | | | | | | | | | Ce | 0.5 | | | | | | | | | | |
| | | | | | | | | | Sm | 0.2 | | | | | | | | | | |
| Comparative Example 1 | 3 | 3.3 | 10 | 0.4 | 0.6 | 0.2 | Ni | 6 | Cr | 0.8 | | | | | P | 0.2 | | | 35 | 1.06 |
| | | | | | | | | | Ce | 0.4 | | | | | B | 0.2 | | | | |
| Comparative Example 2 | 3 | 3.3 | 10 | 0.4 | 1.1 | 0.2 | Ni | 6.0 | | | | | | | P | 0.2 | | | 35 | 1.20 |
| | | | | | | | | | | | | | | | B | 0.2 | | | | |
| Comparative Example 3 | 3 | 3.3 | 10 | 1 | 1.3 | 0.2 | Ni | 5.5 | Cr | 1.5 | | | Ge | 0.2 | B | 0.2 | | | 35 | 0.79 |
| | | | | | | | Zn | 0.2 | Ce | 0.6 | | | | | | | | | | |
| | | | | | | | | | La | 0.2 | | | | | | | | | | |
| Comparative Example 4 | 3 | 3.3 | 10 | 0.4 | 2.0 | 0.2 | Ni | 6 | Cr | 1.5 | | | Ge | 0.2 | B | 0.2 | | | 35 | 0.75 |
| | | | | | | | Zn | 0.2 | Ce | 0.6 | | | | | | | | | | |
| | | | | | | | | | La | 0.2 | | | | | | | | | | |

| | Calcination conditions | | Reaction conditions | | Acrylonitrile yield [%] Time elapsed [hr] | | | Kind of Molybdenum added |
|---|---|---|---|---|---|---|---|---|
| | Temperature [° C.] | Time [hr] | Temperature [° C.] | Contact time [sec] | 50 | 500 | 1000 | |
| Example 1 | 660 | 3 | 440 | 3.0 | 81.9 | 81.8 | 82.0 | Ammonium paramolybdate |
| Example 2 | 640 | 3 | 440 | 3.0 | 82.1 | 81.9 | 81.7 | Molybedenum trioxide |
| Example 3 | 670 | 3 | 440 | 3.2 | 81.6 | 81.5 | 81.5 | Molybdenum-enriched catalyst |
| Example 4 | 650 | 3 | 440 | 3.0 | 81.8 | 81.5 | 81.6 | Molybdenum trioxide |
| Example 5 | 670 | 3 | 440 | 3.5 | 81.3 | 81.1 | 81.0 | Ammonium paramolybdate |
| Example 6 | 670 | 3 | 440 | 3.0 | 81.5 | 81.3 | 81.2 | " |
| Example 7 | 630 | 3 | 440 | 3.2 | 81.2 | 81.4 | 81.3 | Molybdenum-enriched catalyst |
| Example 8 | 610 | 3 | 440 | 3.0 | 81.5 | 81.4 | 81.4 | " |
| Example 9 | 670 | 3 | 440 | 3.5 | 81.4 | 81.2 | 81.2 | " |
| Example 10 | 680 | 3 | 440 | 3.7 | 81.8 | 81.9 | 81.6 | " |
| Comparative Example 1 | 640 | 3 | 440 | 3.0 | 81.9 | 80.5 | 79.2 | Ammonium paramolybdate |
| Comparative Example 2 | 650 | 3 | 440 | 3.2 | 81.5 | 80.7 | 79.4 | " |
| Comparative Example 3 | 670 | 3 | 440 | 3.0 | 81.0 | 80.3 | 78.8 | Molybdenum-enriched catalyst |
| Comparative Example 4 | 690 | 3 | 440 | 3.5 | 81.4 | 80.1 | 79.0 | " |

INDUSTRRIAL APPLICABILITY

The process for producing acrylonitrile in accordance with the present invention can give a high acrylonitrile yield. Moreover, it is possible to increase long-term stability of the reaction owing to a stable catalyst structure, and to maintain the catalyst efficiency for a long period of time by adding and supplying a molybdenum component.

What is claimed is:

1. A process for producing acrylonitrile, comprising:
ammoxidizing propylene in the presence of a fluidized bed catalyst having a composition represented by the following empirical formula

while adding a molybdenum-containing material to obtain said acrylonitrile;
wherein
(Fe Sba) represents iron and antimony forming iron antimonate;
Mo, Bi, Fe and K are molybdenum, bismuth, iron and potassium, respectively;
M is at least one element selected from the group consisting of magnesium, calcium, strontium, barium, manganese, cobalt, nickel, copper, zinc and cadmium;
N is at least one element selected from the group consisting of chromium, yttrium, lanthanum, cerium, praseodymium, neodymium, samarium, aluminum, gallium and indium;
G is at least one element selected from the group consisting of ruthenium, rhodium, palladium, rhenium, osmium, iridium, platinum and silver;
Q is at least one element selected from the group consisting of titanium, zirconium, vanadium, niobium, tantalum, tungsten, germanium, tin, lead and antimony;
R is at least one element selected from the group consisting of boron, phosphorus and tellurium;
T is at least one element selected from the group consisting of lithium, sodium, rubidium, cesium and thallium;
O is oxygen;
Si is silicon; and affixes a, b, c, d, k, m, n, g, q, r, t, x and y are independently of one another an atomic ratio, provided that a=0.8 to 2, b=0.5 to 20, c=0.1 to 2, d=0.3 to 3, k=0.05 to 2, m=3 to 8, n=0.1 to 3, g=0 to 0.5, q=0 to 3, r=0 to 3, t=0 to 1, x is a number of oxygen in a metal oxide formed by bonding of said respective components, y=20 to 200; and a number of Mo/Me is from 0.8 to 1, wherein the Mo/Me is a number obtained by dividing the product, which is 20, of a valence number of molybdenum as molybdic acid and an atomic ratio of molybdenum by the sum of respective products of respective valence numbers and atomic ratios of respective metal molybdate-producible metal elements other than iron antimonate, that is, bismuth, iron, potassium, the M component element, the N component element and the T component element.

2. The process for producing acrylonitrile according to claim 1, wherein the molybdenum-containing material to be added is a molybdenum-enriched catalyst obtained by enriching said fluidized bed catalyst with molybdenum.

3. The process according to claim 1, wherein M is at least one element selected from the group consisting of magnesium, calcium, manganese, cobalt, nickel and zinc; N is at least one element selected from the group consisting of chromium, lanthanum, cerium, praseodymium, neodymium, samarium, aluminum and indium; G is at least one element selected from the group consisting of ruthenium, palladium and silver; Q is at least one element selected from the group consisting of zirconium, vanadium, niobium, tungsten, germanium, tin and antimony; T is at least one element selected from the group consisting of rubidium and cesium; a=0.85 to 1.8, b=0.7 to 15, c=0.2 to 1.5, d=0.5 to 2.5, k=0.1 to 1.5, m=4 to 7, n=0.2 to 2.5, g=0 to 0.2, q=0 to 2, r=0 to 2, t=0 to 0.5, and y=25 to 80.

4. The process according to claim 1, wherein the molybdenum-containing material is added in an amount of from 0.05 to 2% by weight as molybdenum element based on the weight of said fluidized bed catalyst.

5. The process according to claim 2, wherein the molybdenum-containing material is added in an amount of from 0.05 to 2% by weight as molybdenum element based on the weight of said fluidized bed catalyst.

6. The process according to claim 3, wherein the molybdenum-containing material is added in an amount of from 0.05 to 2% by weight as molybdenum element based on the weight of said fluidized bed catalyst.

7. The process according to claim 1, wherein said ammoxidizing is carried out at a temperature exceeding 400° C.

8. The process according to claim 1, wherein said iron antimonate exists as a crystal phase in said catalyst.

9. The process according to claim 1, wherein said molybdenum-containing material comprises a member selected from the group consisting of metal molybdenum, molybdenum trioxide, molybdic acid, ammonium dimolybdate, ammonium paramolybdate, ammonium octamolybdate, ammonium dodecamolybdate, and phosphomolybdic acid.

10. The process according to claim 1, wherein said molybdenum-containing material is in the form of a powder.

11. The process according to claim 1, wherein said molybdenum-containing material is added in a continuous manner.

12. The process according to claim 1, wherein said molybdenum-containing material is added in intervals.

13. The process according to claim 1, wherein said molybdenum-containing material is added in amount of from 0.01 to 3% by weight, as molybdenum element based on a weight of said catalyst, at an interval.

14. The process according to claim 1, wherein said interval is 100 to 500 hours.

* * * * *